US006711434B2

(12) United States Patent
Kramer et al.

(10) Patent No.: US 6,711,434 B2
(45) Date of Patent: Mar. 23, 2004

(54) PHYSIOLOGICAL SENSOR SYSTEM

(75) Inventors: Michael Kramer, Erlangen (DE);
Walter Maerzendorfer, Erlangen (DE);
Ulrich Schaetzle, Strullendorf (DE)

(73) Assignee: Siemens Aktiengesellschaft, Münich (DE)

( * ) Notice: Subject to any disclaimer, the term of this patent is extended or adjusted under 35 U.S.C. 154(b) by 167 days.

(21) Appl. No.: 09/954,890

(22) Filed: Sep. 18, 2001

(65) Prior Publication Data

US 2002/0077560 A1 Jun. 20, 2002

(30) Foreign Application Priority Data

Sep. 25, 2000 (DE) .......................... 100 47 365

(51) Int. Cl.[7] .............................................. A61B 5/04
(52) U.S. Cl. ....................................................... 600/509
(58) Field of Search ................................ 600/481, 490, 600/491, 500, 502, 509, 529, 534, 544; 607/32, 36

(56) References Cited

U.S. PATENT DOCUMENTS

| 4,537,200 A | * | 8/1985 | Widrow ...................... 128/696 |
| 4,679,002 A | * | 7/1987 | Sherwin et al. ................ 330/66 |
| 4,737,712 A | | 4/1988 | Stormont et al. ............ 324/307 |
| 4,763,075 A | | 8/1988 | Weigert ....................... 324/318 |
| 5,052,398 A | | 10/1991 | Gober ......................... 600/509 |
| 5,099,856 A | * | 3/1992 | Killion et al. ............... 128/731 |
| 5,275,159 A | | 1/1994 | Griebel ........................ 600/324 |
| 5,394,873 A | | 3/1995 | Kraemer et al. ............ 600/523 |
| 5,782,241 A | | 7/1998 | Felblinger et al. .......... 600/509 |
| 6,052,614 A | | 4/2000 | Morris, Sr. et al. ......... 600/509 |

* cited by examiner

*Primary Examiner*—Carl Layno
(74) *Attorney, Agent, or Firm*—Schiff Hardin LLP

(57) ABSTRACT

A physiological sensor system is provided for recording electrical measurement signals in an environment which impairs the recording, in particular in a magnetic resonance instrument, having a plurality of measurement electrodes as well as a signal amplifier device, a power supply and an electronic device for signal conversion and signal transmission to an external signal processing and/or control instrument. The measurement electrodes (3, 4, 5, 14, 15, n) and the signal amplifier device (6, 16) are arranged in a first shielded casing (2, 13), and the power supply and the electronic device being arranged in a second shielded casing (9), the signal amplifier device (6, 16) being connected or connectable to the electronic device and the power supply through a shielded and/or twisted-wire cable connection (7, 17).

33 Claims, 6 Drawing Sheets

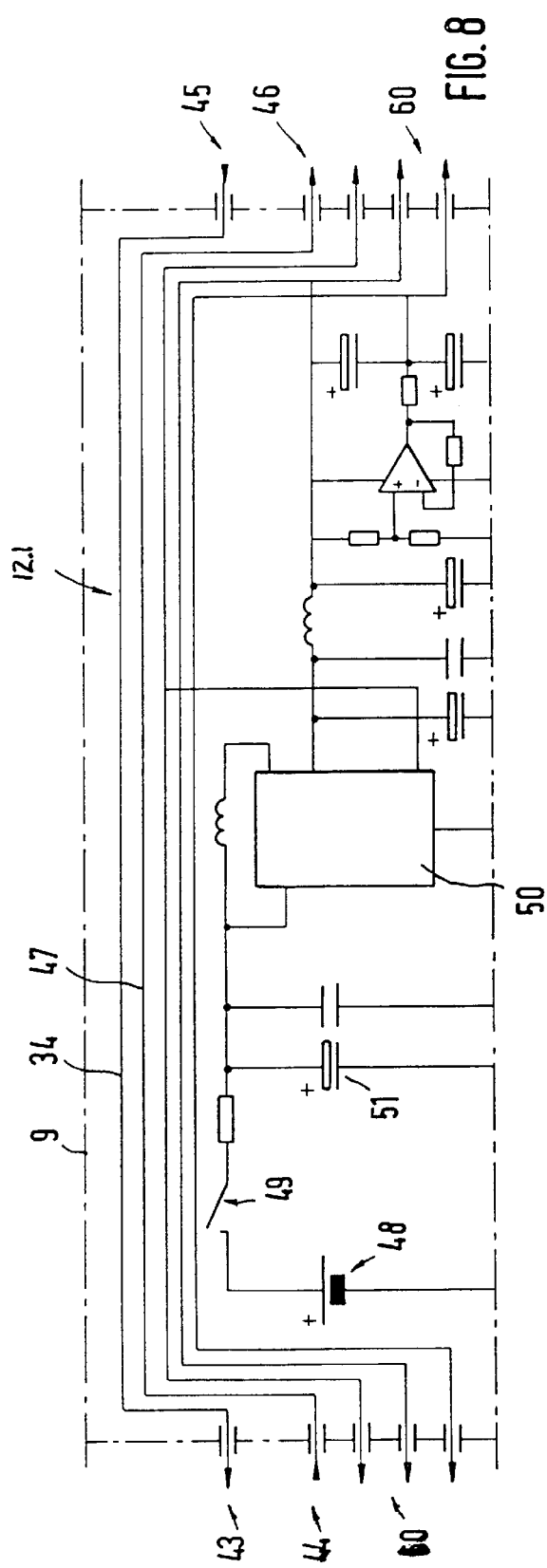
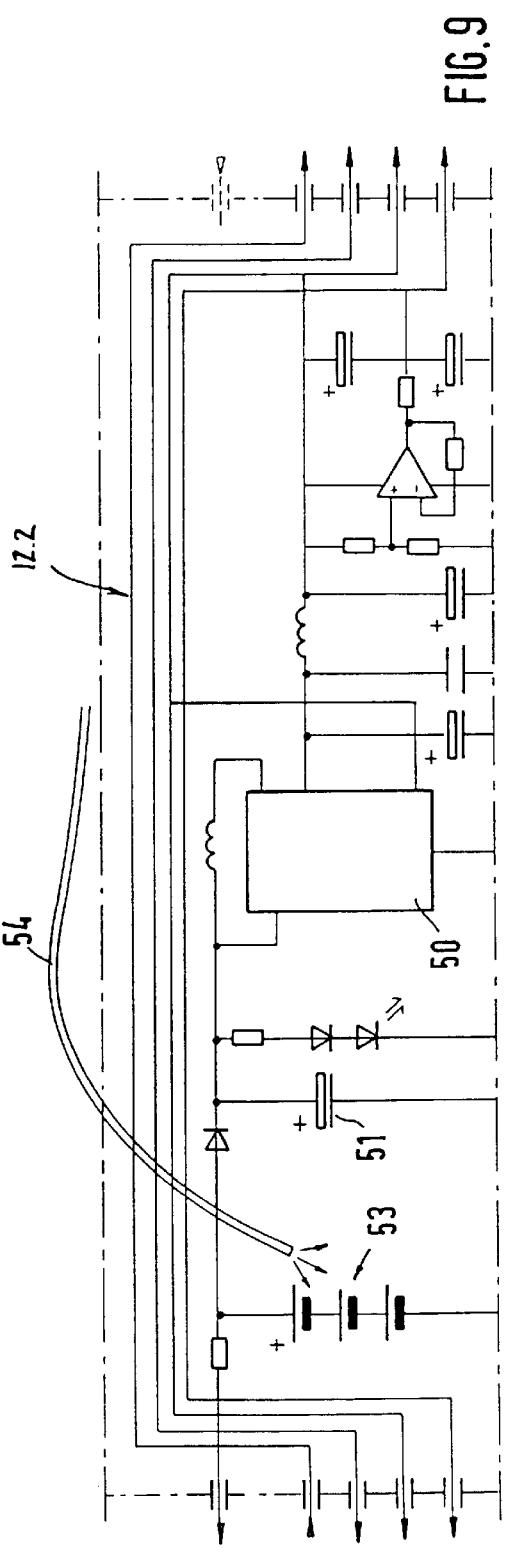

PHYSIOLOGICAL SENSOR SYSTEM

BACKGROUND OF THE INVENTION

1. Field of the Invention

The invention relates to a physiological sensor system for recording electrical measurement signals in an environment which impairs this recording, particularly in a magnetic resonance instrument, having a plurality of measurement electrodes as well as a signal amplifier device, a power supply, and an electronic device for signal conversion and transmission to an external signal processing and/or control instrument.

Such a physiological sensor system is used for the in situ recording of physiological measurement values, for example, during an examination of a patient using a magnetic resonance instrument. By using such a sensor system, it is, for example, possible to record an ECG during the examination so that, on the one hand, the heart activity can be registered continuously and, on the other hand, the imaging of the magnetic resonance instrument can be controlled by continuously registering the heart's position. If the magnetic resonance images show, for example, the heart in a certain valve position, then the moment at which the heart is in the desired valve position can be registered exactly through the ECG signals, and the imaging can be triggered as a result of this information.

2. Description of the Related Art

Such a physiological sensor system is known from U.S. Pat. Nos. 5,782,241 and 6,052,614. In this sensor system, there are a number of measurement electrodes which are applied directly to the patient's skin. The electrodes are arranged at the lower end of a shielded casing. The casing further contains radio frequency filter devices to each of which an electrode is allocated, as well as a differential amplifier unit, a low pass filter, an electro-optical transducer for converting the measurement signals into optical signals that are given through an optical data line to an external processing and display device, as well as a power source in the form of a battery.

All of the elements relevant to the operations of recording and preprocessing the measurement signals are hence arranged together in the casing, which is applied to the patient. However, this is disadvantageous because of the considerable structural size and the simultaneous integration of the measurement electrodes—the sensor system has to be positioned close to the heart. Moreover, this entails the risk that this sensor system lies at least partially in the imaging region, i.e., in the region from which the magnetic resonance image is intended to be recorded. The latter is thereby at least impaired.

European patent document EP 0 173 130 A1 discloses a device for nuclear spin tomography, in which the electrodes are connected through a cable link to an amplifier device located externally to the nuclear spin tomography device. From this amplifier device, which is arranged together with the nuclear spin tomography device in an RF cabin, the measurement signals are given through an optical waveguide with a connection to a processing device located externally to the cabin. German patent document DE 33 27 731 A1 describes a device for obtaining an ECG signal in a nuclear spin tomograph, in which the nuclear spin tomograph is likewise arranged in an RF cabin, the recorded signals being fed through a shielded connection, which is set to the electrical potential of the RF cabin, in order to avoid interference with the NMR image. German patent document DE 198 17 094 describes a method and a device for deriving an electroencephalogram in the nuclear spin tomograph, while U.S. Pat. No. 4,737,712 describes an isolated power source which can operate in a strong magnetic field and an RF field, as may be found, e.g., in an NMR instrument. Lastly, U.S. Pat. No. 5,052,398 describes a filter suitable to be used in an NMR instrument for real-time heart representation, while German patent document DE 41 38 702 A1 describes a method and a device for diagnosis and quantitative analysis of apnoea and for simultaneous identification of other diseases. Lastly, German patent document DE 41 23 578 A1 describes a non-invasive method for spatial registering of local heart potentials.

SUMMARY OF THE INVENTION

It is an object of the invention to provide a physiological sensor system which affects the imaging as little as possible, yet allows minimally distorted recording of the measurement signals.

To achieve this object, in a physiological sensor system of the type mentioned previously, according to the invention, the measurement electrodes and the signal amplifier device are arranged in or on a shielded first sensor casing to be arranged close to the patient, and the power supply and the electronic device are arranged in a second shielded casing to be arranged close to the patient, the signal amplifier device being connected or connectable to the electronic device and the power supply through a shielded and/or twisted-wire cable connection.

The sensor system according to the invention comprises two shielded casings, which are constructed in the manner of a Faraday cage, and which contain the components needed for the measurement value recording and pre-processing. Only the measurement electrodes and the signal amplifier device are present in the shielded first sensor casing. This first sensor casing is applied directly to the patient, in the region near the heart in the case of recording an ECG. Since only the measurement electrodes—generally three—and the signal amplifier device are integrated in this sensor casing, it is very small so that it can be positioned in such a way that exact measurement value recording is possible, although because of its size it does not substantially affect the imaging.

The recorded measurement signals are given through a shielded or twisted-wire cable connection to the second shielded casing, and there to the electronic device and the power supply. The shielded or twisted-wire cable connection ensures that the analog and amplified measurement signals can be transmitted substantially unaffected by the strong magnetic fields which exist during the operation of a magnetic resonance instrument. This means that the signal-to-noise ratio is virtually unchanged. The second casing can then be positioned fully out of the image-relevant examination region. The length of the cable connection should expediently be in the range between 20–30 cm, although it may be greater.

The signal amplifier device should expediently be arranged in immediate proximity to the measurement electrodes so as to minimize the admission of noise signals. If a plurality of measurement electrodes are arranged in the sensor casing, then a common signal amplifier device can be allocated to them. Alternatively, each measurement electrode can be provided with its own amplifier.

Besides a system configuration having one first sensor casing and one second shielded casing, it is also possible for the system to comprise a plurality of sensor casings, each with a plurality of measurement electrodes and an allocated signal amplifier device, different measurement signals being recordable by the measurement electrodes of a respective sensor casing, and each signal amplifier device being connected or connectable to the common electronic device and the common power supply through a separate shielded or twisted-wire cable connection. In this multifunctional sensor system, for example, one first sensor casing can be used to record ECG measurement signals and the other sensor casing can be used to record EEG measurement signals. Both are very small, since they only contain the electrodes and the amplifier device, and the common signal preparation takes place in the common second shielded casing.

It is particularly expedient for the signal amplifier device, in the case of measurement electrodes intended to record ECG measurement signals, to be designed just to amplify the measurement signals. As an alternative to this, it is possible for the amplifier device also to be designed to form leadoff-specific differential signals. In the scope of an ECG measurement, which corresponds to the extremity leadoffs according to Einthoven, three measurement electrodes are used which are oriented in different directions. A first measurement electrode goes to the left arm, a second to the right arm and a third to the left leg. Differential signals between two measurement electrodes are respectively recorded as ECG measurement signals. Each differential signal corresponds to one leadoff, three leadoffs being possible in all, namely, the first differential signal of the measurement electrodes "left arm-right arm", the second differential signal "left leg-right arm" and the third differential signal "left leg-left arm". For technical processing reasons, it is expedient if this difference formation is already carried out on the part of the amplifier device. Operational amplifiers are expediently used for the amplification and/or differential signal formation.

The electronic device itself expediently has a signal conversion module and a signal transmission module, both of which are coupled to the power supply. The term "module" is here used very generally to denote a circuit arrangement with the smallest possible dimensioning, which is used for either the signal conversion or the signal transmission. All the elements needed for this can be arranged on a common board. Since, naturally, it is also desirable for the second shielded casing to be dimensioned as small as possible, common integration of the modules is expedient.

The signal conversion module should expediently have at least one filter and at least one converter unit. An analog/digital converter or a voltage/frequency converter can be used as converters.

If a plurality of measurement signal inputs are provided at the second shielded casing, or at the electronic device, then it is expedient for a separate filter to be provided for each measurement input, the filters being connected to the converter through a multiplexer. A filter is expediently provided for each measurement signal input, irrespective of the type of the measurement signals which are delivered, i.e., whether they are, for example, ECG or EEG measurement signals which can be registered together and read out in multiplex operation. The operation of the multiplexer can expediently be controlled externally through a control line, so that the signal recording can be controlled externally through an external signal processing and/or control instrument.

The power supply can have a battery, or an accumulator to which a switch that can be actuated through an external magnetic field is allocated. This configuration is expedient so long as, during operation of the magnetic resonance instrument, a sufficient magnetic field is applied so that the switch is actuated and the supply circuit is closed. As soon as the sensor system has been removed from the magnetic resonance instrument, the switch re-opens and the power supply is hence not kept continuously on.

As an alternative to this, the power supply can also contain one or more solar cells which can be illuminated with light that can be fed through an optical fiber, particularly laser light. According to a third alternative of the invention, the power supply contains one or more solar cells which can be illuminated with light that can be fed through a fluorescence collector, which is arranged on the outside of the casing and captures ambient light. Such a fluorescence collector may be a plate material made of polymethyl methacrylate, into which fluorescein and other fluoropolymers are polymerized. This collector gathers incident diffuse ambient light, which is concentrated on its end face and emerges through a narrow region. According to the invention, this concentrated light strikes the solar cell configuration which in turn generates energy.

Lastly, according to a fourth alternative of the invention, the power supply contains at least one capacitor which is connected to coils that are arranged on the outside of the casing and deliver a voltage when an external magnetic field is applied. This configuration according to the invention utilizes the magnetic field which is applied anyway during operation of the magnetic resonance instrument, by the fact that, on the outside of the casing, coils are arranged in which the magnetic field leads to the induction of an AC voltage, which is used after rectifying to charge a capacitor that then supplies the individual system elements with power.

It has been found to be particularly advantageous if at least one storage capacitor, having a storage capacitance$\geq 1$ F, which provides power during operation, is allocated to the solar cells. This storage capacitor which, in the field, is known as "Ultra Cap" or "Gold Cap", has a relatively high capacitance and can hence store a sufficient amount of power, which it then gives out during operation. This ensures that the system elements are only supplied with voltage when the power delivered by the solar cells, or by the at least one capacitor connected to the coils, is not sufficient. The storage capacitor can expediently be recharged in an external charging station. When solar cells are used, the charging station would generate maximally energetic light in order to guarantee a short charging time.

The signal transmission module can, according to a first configuration of the invention, be a radio transmission module, with which the recorded, amplified and subsequently converted measurement signals can be transmitted wirelessly to the external processing device.

According to an alternative embodiment, however, the signal transmission module may be an infrared transmission module having at least one infrared transmission diode with an allocated optical line that leads from the casing but not to the receiver, in which case a plurality of diodes, in particular three, to each of which an optical line is allocated, may expediently be provided.

According to a third configuration of the invention, the signal transmission module can be a fiber optic transmission module having at least one transmission diode with an allocated fiber optic line. Lastly, a fourth alternative embodiment provides that the signal transmission module be an ultrasonic wave module having at least one ultrasound transducer.

It is expedient for the multiplexer to be externally controllable. To that end, an input for the external control line can be provided at the signal transmission module, the control signals being looped through internal control lines from the signal transmission module to the signal conversion module, optionally through the power supply. In this case, it is expedient for an optical receiver, which transforms the optical control signals provided through the optical control line into electrical control signals, to be allocated to the internal control line provided at the signal transmission module. According to a second alternative, in the case of a configuration of the signal transmission module as an ultrasonic wave module, the ultrasound signal line is also used to transmit the control signals, so that it is used simultaneously as a forward and return line. The control signals are transformed by the ultrasound transducer into electrical control signals, which are then forwarded through the internal control line.

As described, it is possible to provide a plurality of sensor casings for recording different electrical measurement signals in the sensor system according to the invention. In order to increase the multifunctionality of the sensor system yet further, it has been found to be expedient that at least one further sensor element, which registers non-electrical measurement information, also be connected or can be connected to the second shielded casing, the electronic device having a corresponding mechanism for converting the non-electrical measurement information into electrical measurement signals. As a further sensor element, it is possible to provide an optical sensor element, particularly a finger ring which, for example, is placed around a patient's finger and measures the patient's peripheral pulse by transmitted illumination and absorption measurement. This optical sensor element delivers optical measurement information which is sent through a fiber optic line to the electronic device, where an optoelectronic converter for conversion into electrical measurement signals is provided. As an alternative, the at least one further sensor element can be a pneumatic sensor element, particularly a flexible chest ring, which is placed around the patient's chest and by way of which the respiratory activity can be measured. This chest ring has a compressible air volume, which is coupled to the electronic device through a pressure line having a pressure sensor. Since, due to breathing, the air volume and therefore the pressure change, the pressure sensor experiences a continuously changing pressure, which can be converted into corresponding electrical measurement signals.

DESCRIPTION OF THE DRAWINGS

Further advantages, features and details of the invention can be found in the exemplary embodiments described below and with the aid of the drawings.

FIG. 8 is a circuit schematic showing the power supply device in the second shielded casing according to a first embodiment;

FIG. 9 is a circuit schematic showing the power supply module in the second shielded casing according to a second embodiment;

DETAILED DESCRIPTION OF THE INVENTION

Figure 1:
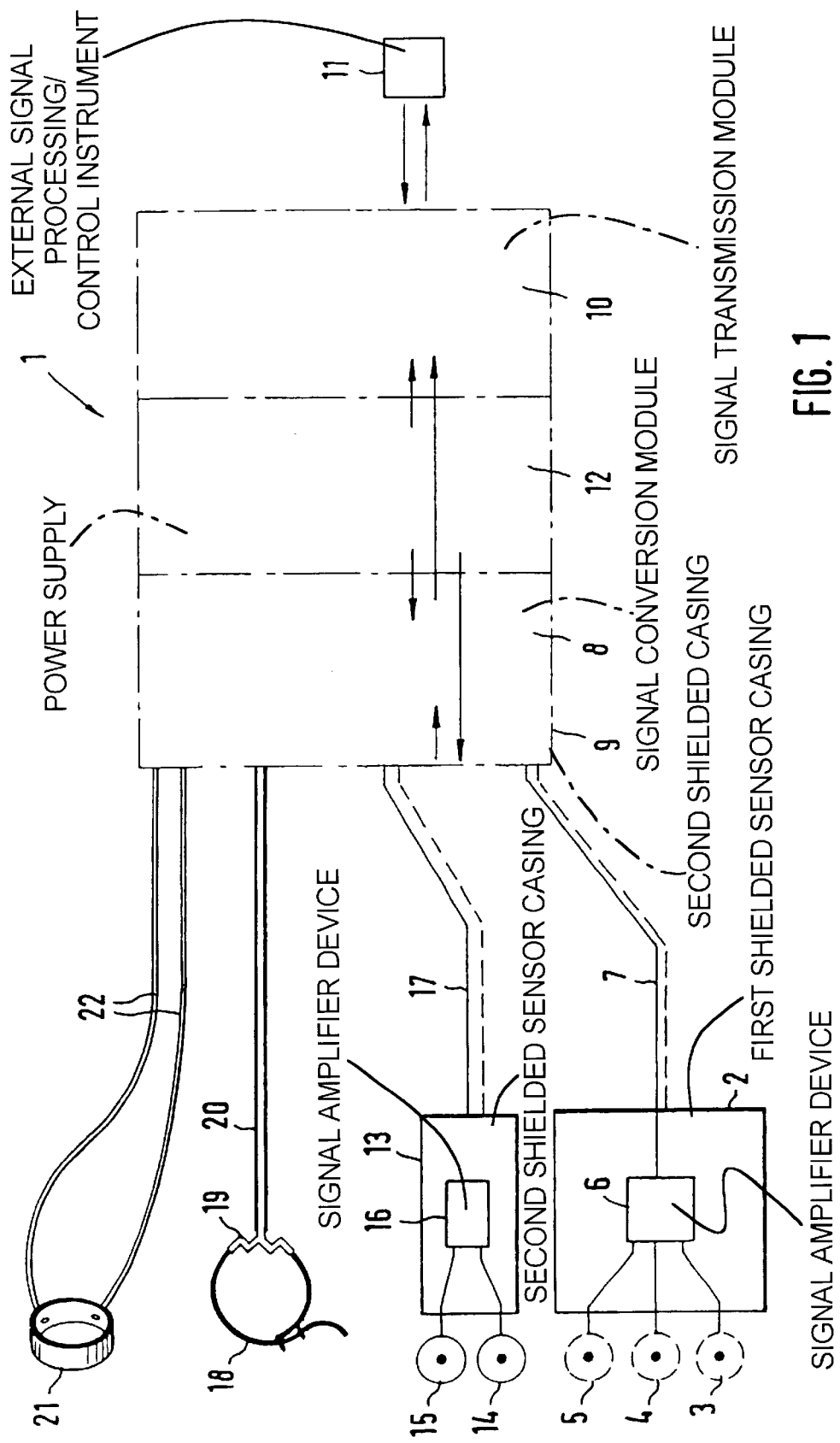
FIG. 1 is a schematic block diagram showing a basic representation of a sensor system according to the invention.

FIG. 1 is a basic representation of a physiological sensor system 1 according to the invention. The sensor system comprises a first sensor casing 2 on which, in the example shown, three electrodes 3, 4, 5 are arranged that, for example, are designed to record an ECG. A signal amplifier device 6, which amplifies the signals delivered through the electrodes 3, 4, 5, is furthermore arranged in the first sensor casing 2. The measurement signals are given through a shielded or twisted-wire cable connection 7 to a signal conversion module 8, which is arranged in a second shielded casing 9. There, the signals are converted and subsequently given through a signal transmission module 10 to an external signal processing and/or control instrument 11. A power supply 12, which supplies the entire sensor system with power, is furthermore arranged in the second shielded casing 9.

As FIG. 1 also shows, a second sensor casing 13 may be provided, on which two electrodes 14, 15 can likewise be arranged in the example shown. These are designed, for example, to record EEG measurement signals. Of course, more than two electrodes can also be provided. A signal amplifier device 16, which amplifies the signals in situ, i.e., immediately at the measurement site, is also arranged in this shielded sensor casing 13. These measurement signals are also given through a shielded or twisted-wire cable connection 17 to the signal conversion module 8, and correspondingly prepared.

A further sensor element 18 which, in the exemplary embodiment shown is a flexible chest ring (through which the patient's breathing can be recorded) is furthermore connected to the second shielded casing 9. This sensor element 18 comprises a compressible air volume 19 which is compressed or expanded correspondingly as the thorax rises and falls. The changing pressure is given through a pneumatic connection line 20 to a corresponding sensor in the signal conversion module 8, which is discussed in further detail below. A second sensor element 21, in the form of a finger ring, is furthermore connected to the second casing 9, by way of which the patient's peripheral pulse can be measured through IR absorption by the blood. The recorded non-electrical measurement information (the information recorded by way of the sensor element 18 is also non-electrical measurement information) is here given through fiber optic lines 22 to a corresponding sensor element in the signal conversion module 8.

Figure 2:
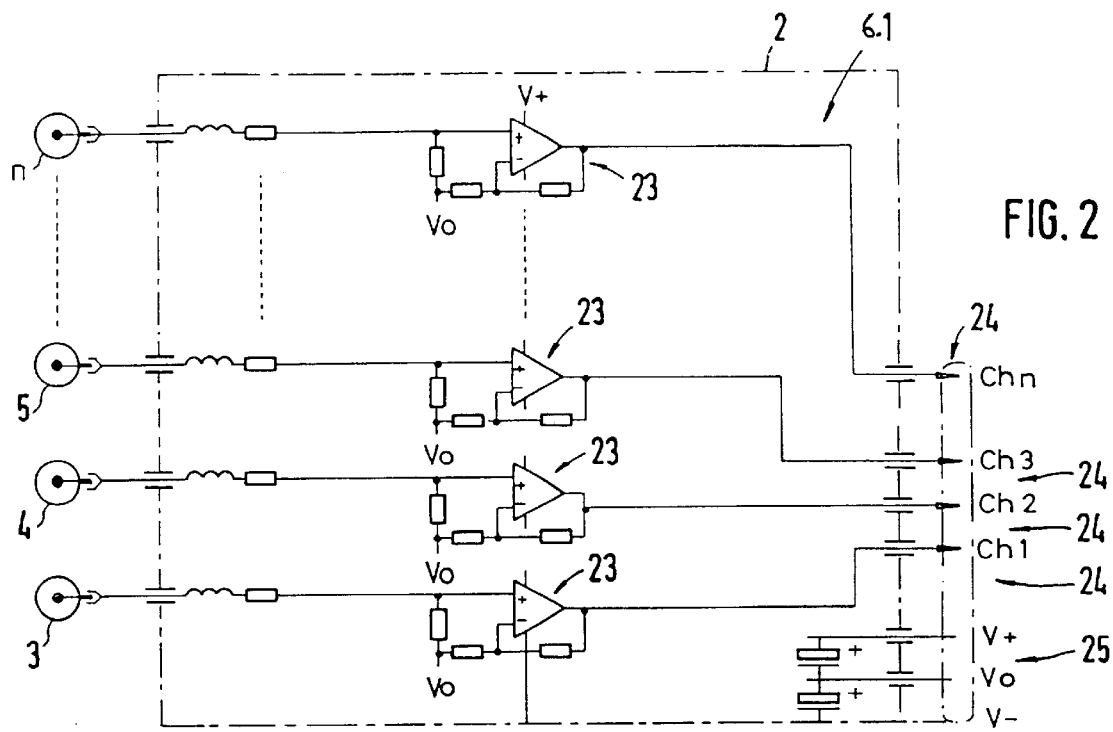
FIG. 2 is a circuit schematic showing a basic representation of the shielded first sensor casing with the signal amplifier device.

FIG. 2 shows the shielded first sensor casing 2 with a circuit arrangement of a first embodiment as an enlarged basic sketch. The electrodes 3, 4, 5 are represented in the example shown, it also being possible to connect more (up to "n") electrodes. An operational amplifier 23, which is used to amplify the measurement signals, is allocated to each electrode 3, 4, 5, ..., n. The amplified measurement signals are provided to corresponding signal outputs 24, which are respectively labelled as Ch1, Ch2, ..., Chn. The inputs 25 for the power supply are also shown.

Figure 3:
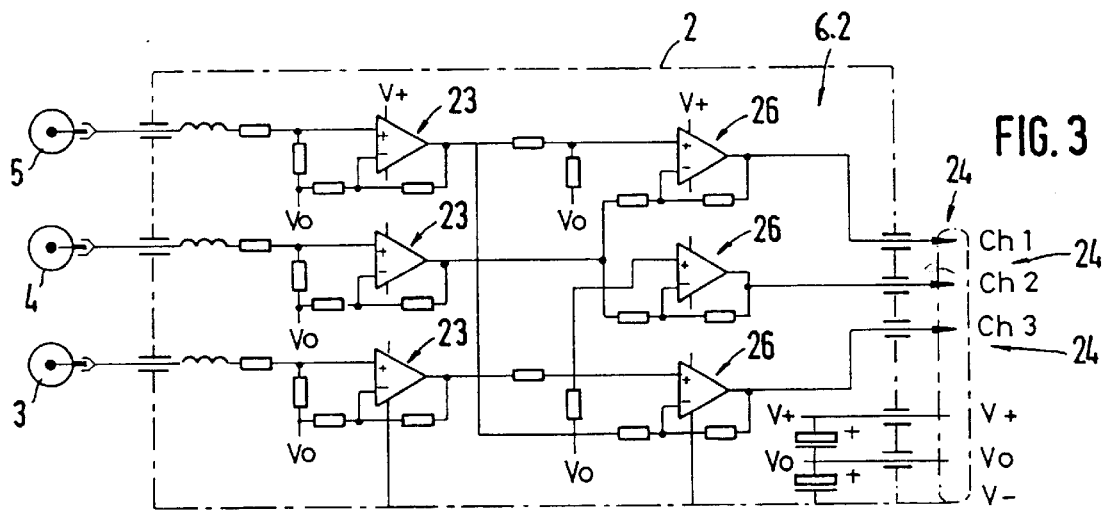
FIG. 3 is a circuit schematic showing a second embodiment of the shielded first sensor casing with the signal amplifier device.

A second embodiment of a first sensor casing with a signal amplifier device is shown in FIG. 3. Three electrodes 3, 4, 5, downstream of each of which an operational amplifier 23 is also connected, are again provided at the sensor casing 2. The signal amplifier device according to FIG. 3 comprises, in addition to the operational amplifiers 23, further operational amplifiers 26 which are interconnected with the operational amplifiers 23 in such a way that a leadoff-specific differential signal is output through the outputs 24. Because of the orientation of the three electrodes 3, 4, 5, three leadoffs are possible in all, namely "left arm-right arm", "left leg-right arm" and "left leg-left arm". The pre-processed differential signals are hence output directly at this point, in contrast to the embodiment according to FIG. 2, where the amplified actual signals are output. The output or transmission respectively takes place through the shielded cable connection.

Figure 4:
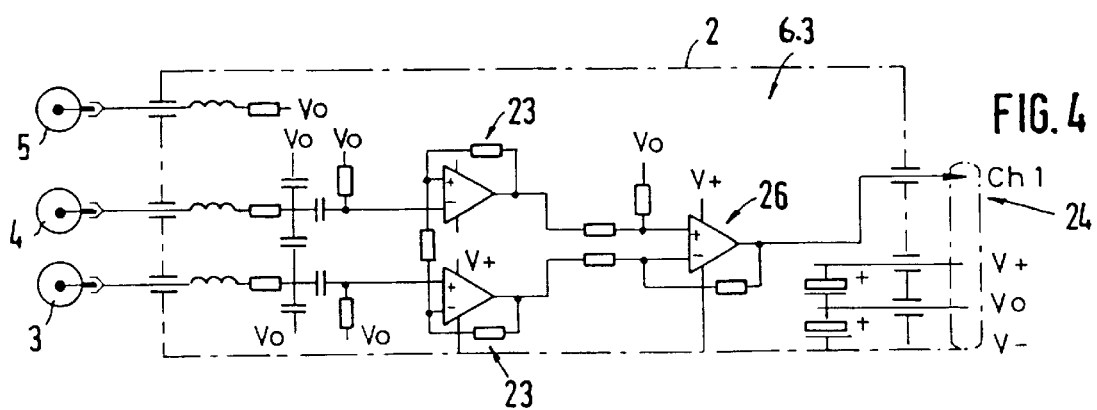
FIG. 4 is a circuit schematic showing a third embodiment of the shielded first sensor casing.

Lastly, FIG. 4 shows a further embodiment of a first sensor casing 2 according to the invention. In this case, three electrodes 3, 4, 5, which are adhesively bonded to the patient and can be positioned according to the desired leadoff, are arranged at this sensor casing 2 not in a fixed way, but rather through short cable connections so that they can move. The electrodes 3 and 4 are used for the measurement signal recording, and the electrode 5 is grounded and is used as a reference. As can be seen, an operational amplifier 23 as well as a common second operational amplifier 26 for the differential signal formation are also connected downstream of each electrode 3, 4 here. Since only a signal between the two electrodes 3, 4 is determined here, only one signal output 24 is provided on this case.

Figure 5:
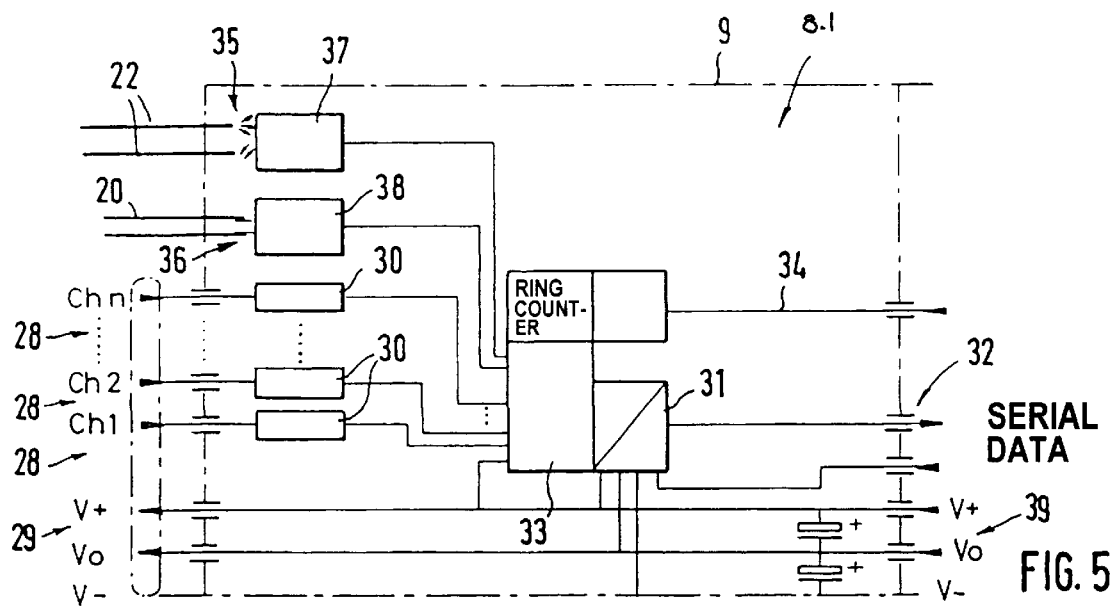
FIG. 5 is a schematic block diagram showing the signal conversion module in the second shielded casing according to a first embodiment.

FIG. 5 shows a first exemplary embodiment of the signal conversion module 8.1, which is arranged in the second shielded casing 9. The amplified signals or the differential signals delivered through the outputs 24 are applied to the inputs 28, and the outputs 29 are used for looping the supply voltage through.

In the example shown, a filter 30 is connected downstream of each of the inputs 28, the filter possibly being a slew rate filter (e.g., according to European patent document EP 0 173 130), in order to filter the signals from noise. The analog signals are converted through a converter 31, which can be an analog/digital converter or a voltage/frequency converter, into digital signals which are output to a subsequent module through the serial output 32. The various inputs are operated in multiplex operation through a multiplexer 33, the multiplexer 33 being controllable by the operator through a control line 34 so that any signals can be read out as desired.

FIG. 5 furthermore shows the inputs 35, 36 to which the signal lines of the further sensor elements 18 and/or 21 are applied. The fiber optic lines 22 transmit their signals to an optoelectronic converter 37, which converts the optical signals into electrical measurement signals, the optoelectronic converter 37 being again connected to the multiplexer 33. The pressure signals, which are fed through the pressure line 20, are given to a pressure sensor 38, which likewise outputs electrical signals and which is also connected to the multiplexer 33. FIG. 5 furthermore represents the corresponding inputs 39 for the looped-through supply voltage.

Figure 6:
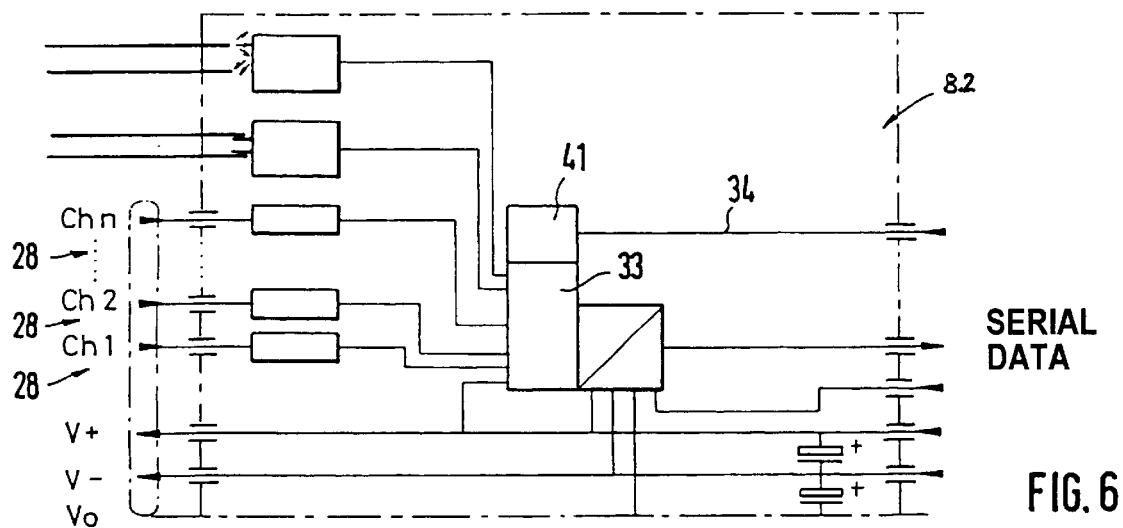
FIG. 6 is a schematic block diagram showing a representation of the signal conversion module of a second embodiment.

A second alternative according to the invention for the signal conversion module is shown by FIG. 6. The structure corresponds substantially to the signal conversion module 8.1, except that the signal conversion module 8.2 according to FIG. 6 has, allocated to the multiplexer 33, a decoder device 41 which controls the multiplexer in such a way that the correct differential signals of the desired leadoff are output. While the signal conversion module 8.1 can be combined with the first sensor casing according to FIG. 2, the signal conversion module 8.2 can be combined with the first casing according to FIG. 3.

Figure 7:
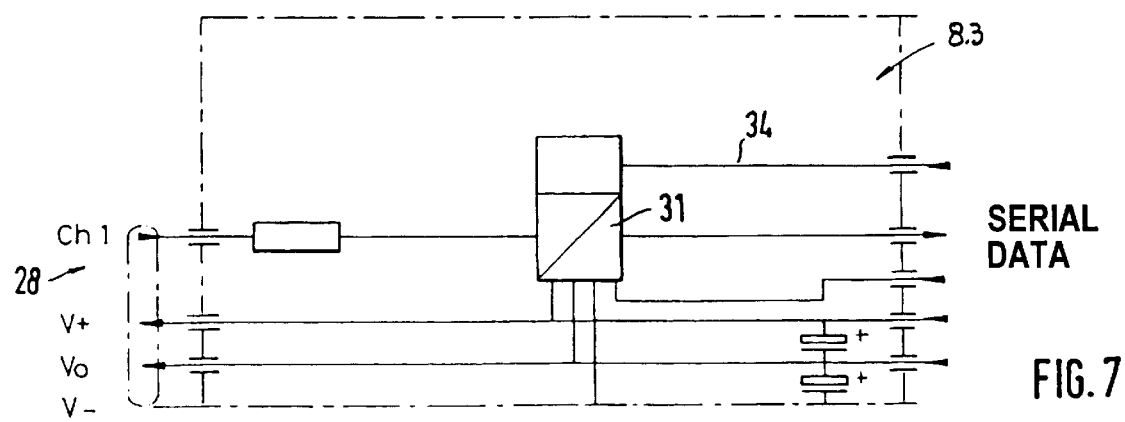
FIG. 7 is a schematic block diagram showing a representation of the signal conversion module of a third embodiment.

A signal conversion module 8.2, which can be combined with the first casing according to FIG. 4, is shown by FIG. 7. Since there is only one input channel 28 here, this signal can be given directly, without the interposition of a multiplexer, to the converter 31 which can likewise be controlled through a control line 34.

FIG. 8 shows a power supply 12.1 of a first embodiment which is arranged in the second shielded casing 9. Through corresponding inputs and outputs 43, 44 and 45, 46, respectively, the converted serial data is looped through this power supply module via a data line 47, or the control signals are looped through it via the control signal line 34. Since this module is only used for the power supply, no signal treatment takes place here.

The power supply 12.1 comprises a battery 48 that can be switched on and off through a switch 49, expediently a reed switch, which can be activated through an external magnetic field. This means that the power supply is switched on automatically through the external magnetic field whenever the patient is in the magnetic resonance instrument and the latter is turned on, and is correspondingly switched off whenever the patient leaves the instrument. A DC—DC converter 50, with a corresponding allocated circuit arrangement, is furthermore allocated to the battery 48, the attached circuit arrangement being intended, inter alia, for the medium voltage generation for the operational amplifiers, the medium voltage being used for symmetry purposes. The DC—DC voltage converter itself makes a regulated voltage from the unregulated voltage of the battery. The converter receives the voltage to be regulated through a capacitor 51, which is charged through the battery 48 and provides a smoothed voltage.

FIG. 9 shows a second embodiment of a power supply 12.2. The structure corresponds essentially to the power supply according to FIG. 8, except that a plurality of solar cells 53 that are illuminated with light, preferably laser light, which is fed from outside through a fiber optic line 54, are provided here for the voltage generation. The voltage generated by the cells 53 again charges a capacitor 51 whose voltage is converted to a constant voltage through a downstream DC—DC converter 50.

Figure 10:
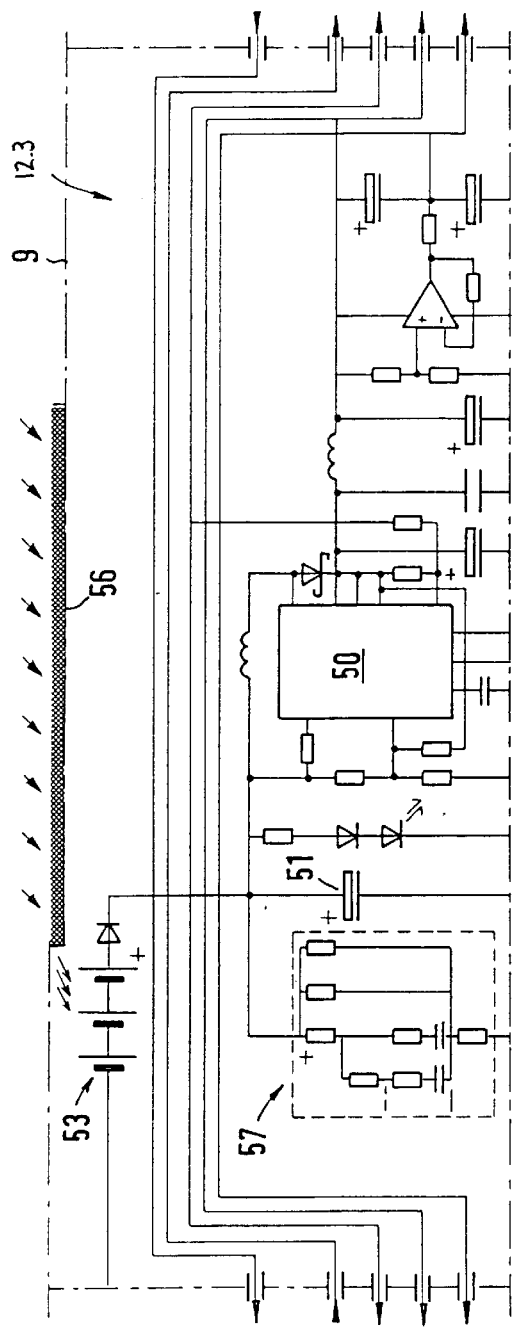
FIG. 10 is a circuit schematic showing the power supply module of the second shielded casing according to a third embodiment.

A third embodiment of a power supply 12.3 according to the invention is shown by FIG. 10, which also provides plurality of solar cells 53. These solar cells 53 are illuminated in this exemplary embodiment with light that is collected and concentrated through a fluorescence collector 56, which is arranged on the outside of the shielded second casing 9. A capacitor 51 is also charged through the solar cell voltage here. The basic structure corresponds to that of the power supplies according to FIGS. 8 and 9. In addition, however, a storage capacitor 57 is allocated here, which has a high capacitance of $\geqq 1$ F and which can be charged in an external charging station before the sensor system is used, although it is additionally charged by the solar cells during operation. This high power capacitor ensures that the capacitor 51 is always charged, even if—for whatever reason—the solar cell voltage drops or is too low. Such capacitors are known in the trade by the names "Ultra Cap" or "Gold Cap".

Figure 11:
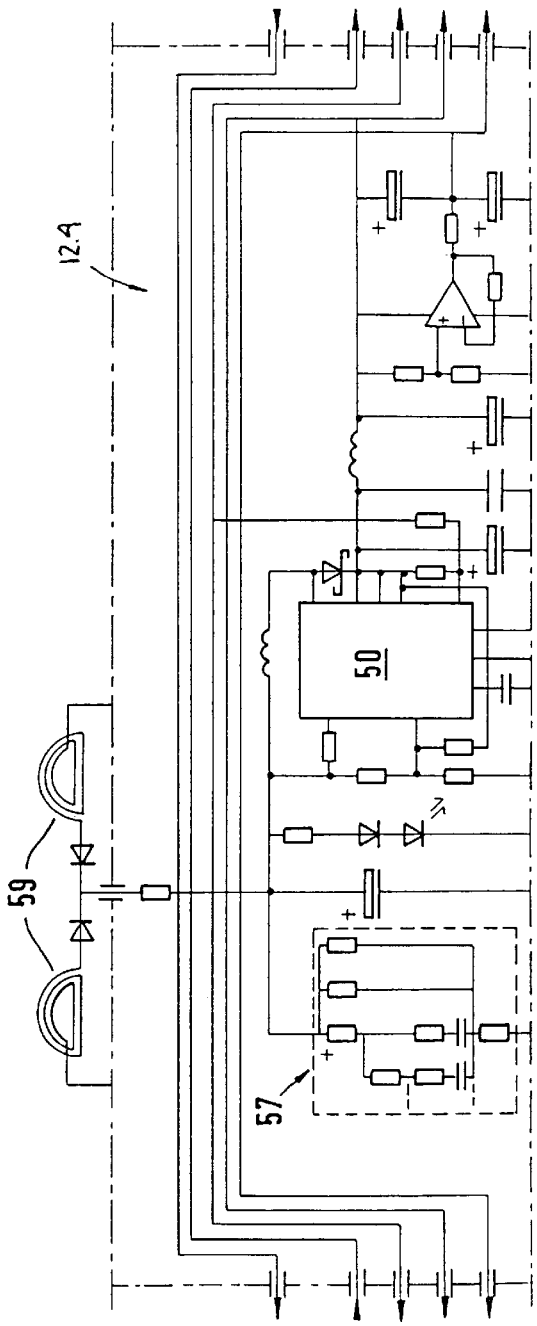
FIG. 11 is a circuit schematic showing the power supply module in a fourth embodiment in the second casing.

A fourth embodiment of a power supply 12.4 is shown by FIG. 11. The capacitors 57 and 51 are here supplied with voltage through two or more induction coils 59 arranged on the outside of the casing. During operation, the applied magnetic field of the magnetic resonance instrument induces, in the coils 59, a voltage which is used to charge the capacitors 57 and 51.

The inputs and outputs, as described with reference to FIG. 8, are also provided in the individual power supplies according to FIGS. 9–11. Corresponding voltage outputs 60 are provided on both sides of the respective power supply, in order to supply the corresponding modules connected to the respective power supply.

Figure 12:
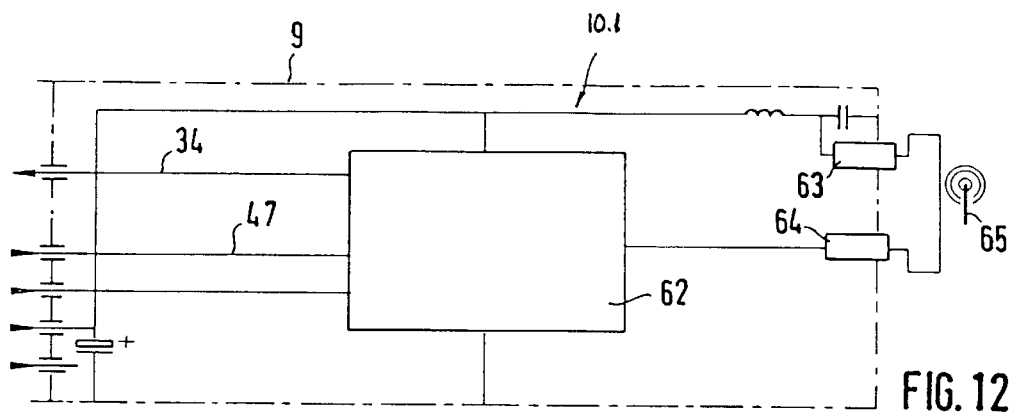
FIG. 12 is a circuit schematic showing the signal transmission module of the second shielded casing according to a first embodiment.

FIG. 12 shows a first embodiment of a signal transmission module 10.1, which is arranged in the second shielded casing 9. The signal transmission module is designed as a radio transmission module and comprises a central transmitter/receiver unit 62, to which the incoming serial data are given through the signal line 47. The externally provided control signals are provided to the respective subsequent module, e.g., to one of the power supply modules shown in FIGS. 8–11 through the signal line 34. The transmitter/receiver unit 62 is coupled through suitable low pass and high pass filters 63, 64 to an RF antenna 65, through which the recorded measurement signals are given to the external signal processing and/or control instrument 11. External control signals, which are forwarded through the control signal line 34, can also be correspondingly received through the RF antenna 65.

Figure 13:
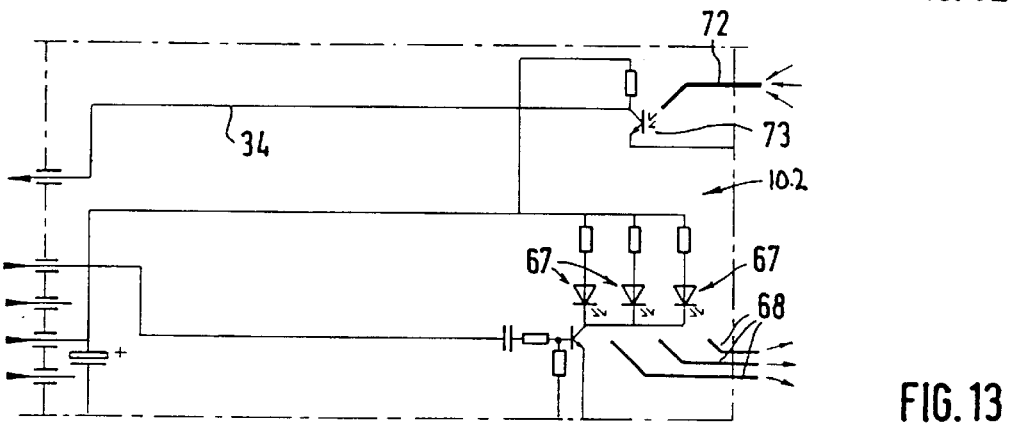
FIG. 13 is a circuit schematic showing the signal transmission module of the second casing of a second embodiment.

A second embodiment is represented in FIG. 13. The signal transmission module 10.2 is designed as an infrared transmission module and comprises three infrared transmission diodes 67, each one of which is respectively allocated to a specific electrode signal. An optical line 68, into which the infrared signals can be injected and through which the signals are transmitted to the external signal processing and/or control instrument 11, are respectively allocated to the infrared transmission diodes 67.

FIG. 13 furthermore shows another possible way in which control signals can be transmitted to the sensor system 1. An optical line 72 is shown through which the control signals (e.g., IR signals) are given to a reception sensor 73 (e.g., an IR phototransistor) where the optical signals are converted into corresponding electrical control signals that can be forwarded through the control signal line 34.

Figure 14:
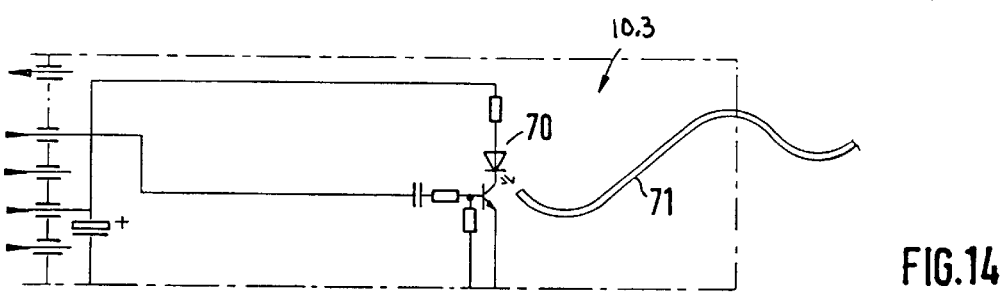
FIG. 14 is a circuit schematic showing the signal transmission module of the second casing of a third embodiment.

FIG. 14 shows a third embodiment of a signal transmission module 10.3 according to the invention. It is designed as a fiber optic transmission module and comprises only one transmission diode 70, to which a fiber optic line 71 is allocated.

Figure 15:
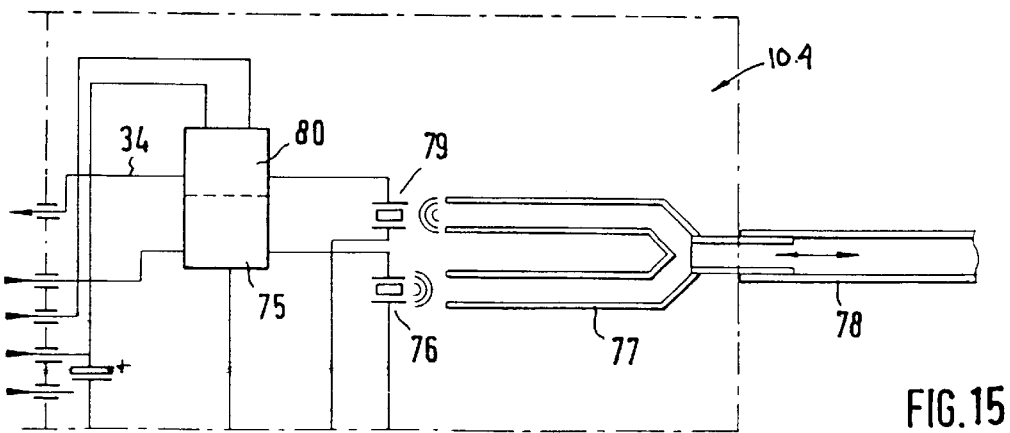
FIG. 15 is a circuit schematic showing the signal transmission module of a fourth embodiment.

A last embodiment of a signal transmission module 10.4 according to the invention is shown by FIG. 15. The serial measurement signals are here given to an oscillator 75, which drives a first ultrasound transducer 76 and through which the electrical measurement signals are converted into acoustic signals. These acoustic signals are forwarded through a sound signal line 77, which is coupled to a sound signal line 78 that passes the signals on to the external signal processing and/or control instrument, where the signals are again converted and further processed. Corresponding acoustic control signals can also be fed through this line 78, and then can be provided through a second branch of the sound-wave line 77 to a second ultrasound transducer 79, where the sound waves are again converted into electrical signals. The converted signal is then given to the control signal line 34 through an ultrasound detector 80.

All the circuit arrangements that have been represented above are only exemplary embodiments, and do not imply any limitation. It is the prerogative of the person skilled in the art to simplify the circuit arrangements, develop them further or combine them suitably.

What is claimed is:

1. A physiological sensor system for recording electrical measurement signals in an environment which impairs recording, comprising:
    a plurality of measurement electrodes;
    a signal amplifier device connected to one or more of said measurement electrodes;
    a power supply;
    an electronic device comprising a signal conversion device and an electronic signal transmission device that transmits to at least one of an external signal processing and a control instrument;
    a first shielded sensor casing arranged close to a patient having the following elements in or on said first shielded sensor casing: said measurement electrodes and said signal amplifier device, but not said power supply; and
    a second shielded casing separate from said first shielded sensor casing arranged close to said patient having the following elements in said second shielded casing: said power supply and said electronic device, said signal amplifier device being connected or connectable to said electronic device and said power supply through at least one of a shielded cable connection and a twisted-wire cable connection.

2. The physiological sensor system as claimed in claim 1, wherein said signal amplifier device is arranged in immediate proximity to said measurement electrodes.

3. A physiological sensor system for recording electrical measurement signals in an environment which impairs recording, comprising:
    a plurality of measurement electrodes;
    a signal amplifier device connected to one or more of said measurement electrodes;
    a power supply;
    an electronic device comprising a signal conversion device and an electronic signal transmission device that transmits to at least one of an external signal processing and a control instrument;
    a first shielded sensor casing arranged close to a patient having the following elements in or on said first shielded sensor casing: said measurement electrodes and said signal amplifier device;
    a second shielded casing arranged close to said patient having the following elements in said second shielded casing: said power supply and said electronic device, said signal amplifier device being connected or connectable to said electronic device and said power supply through at least one of a shielded cable connection and a twisted-wire cable connection; and additional shielded sensor casings, each with a plurality of measurement electrodes and an allocated signal amplifier device, different measurement signals being recordable by measurement electrodes of a respective sensor casing, and each signal amplifier device being connected or connectable to said electronic device and said power supply through at least one of a separate shielded cable connector and a twisted-wire cable connection.

4. The physiological sensor system as claimed in claim 3, wherein one of said measurement electrodes of one of said sensor casings are configured to record EGG measurement signals and another of said measurement electrodes of another of said sensor casings are configured to record EEG measurement signals.

5. A physiological sensor system for recording electrical measurement signals in an environment which impairs recording, comprising:

a plurality of measurement electrodes;

a signal amplifier device connected to one or more of said measurement electrodes;

a power supply;

an electronic device comprising a signal conversion device and an electronic signal transmission device that transmits to at least one of an external signal processing and a control instrument;

a first shielded sensor casing arranged close to a patient having the following elements in or on said first shielded sensor casing: said measurement electrodes and said signal amplifier device; and a second shielded casing arranged close to said patient having the following elements in said second shielded casing: said power supply and said electronic device, said signal amplifier device being connected or connectable to said electronic device and said power supply through at least one of a shielded cable connection and a twisted-wire cable connection;

wherein said signal amplifier device is configured, when at least one of said measurement electrodes is configured to record ECG measurement signals, to amplify measurement signals or to form leadoff-specific differential signals.

6. The physiological sensor system as claimed in claim 5, further comprising operational amplifiers for at least one of said amplification and said differential signal formation.

7. A physiological sensor system for recording electrical measurement signals in an environment which impairs recording, comprising:

a plurality of measurement electrodes;

a signal amplifier device connected to one or more of said measurement electrodes;

a power supply;

an electronic device comprising a signal conversion device and an electronic signal transmission device that transmits to at least one of an external signal processing and a control instrument;

a first shielded sensor casing arranged close to a patient having the following elements in or on said first shielded sensor casing: said measurement electrodes and said signal amplifier device; and a second shielded casing arranged close to said patient having the following elements in said second shielded casing: said power supply and said electronic device, said signal amplifier device being connected or connectable to said electronic device and said power supply through at least one of a shielded cable connection and a twisted-wire cable connection;

wherein said signal conversion device is a signal conversion module and wherein said signal transmission device is a signal transmission module, both of which are coupled to said power supply.

8. The physiological sensor system as claimed in claim 7, wherein said signal conversion module comprises at least one filter and at least one converter unit.

9. The physiological sensor system as claimed in claim 8, wherein said converter unit is an analog/digital converter or a voltage/frequency converter.

10. The physiological sensor system as claimed in claim 8, further comprising:

separate filters provided for each measurement signal input; and a multiplexer connecting said converter unit to said at least one filter and said separate filters.

11. The physiological sensor system as claimed in claim 10, further comprising a control line permitting controlling operation of said multiplexer.

12. The physiological sensor system as claimed in claim 7, wherein said power supply comprises a battery or an accumulator to which a switch that can be actuated through an external magnetic field is allocated.

13. The physiological sensor system as claimed in claim 7, further comprising an optical fiber, said power supply comprising one or more solar cells which can be illuminated with light that can be fed through said optical fiber.

14. The physiological sensor system as claimed in claim 13, further comprising at least one storage capacitor having a capacitance $\geq 1$ F which provides power during operation and can be recharged by said one or more solar cells during operation, said at least one storage capacitor being allocated to said solar cells or to said at least one capacitor.

15. The physiological sensor system as claimed in claim 14, further comprising a external charging station at which said storage capacitor can be charged.

16. The physiological sensor system as claimed in claim 7, further comprising a fluorescence collector arranged on an outside position of said second shielded casing and captures ambient light, said power supply comprising one or more solar cells which can be illuminated with light that can be fed through said fluorescence collector.

17. The physiological sensor system as claimed in claim 16, further comprising at least one storage capacitor having a capacitance $\geq 1$ F which provides power during operation and can be recharged by said one or more solar cells during operation, said at least one storage capacitor being allocated to said solar cells or to said at least one capacitor.

18. The physiological sensor system as claimed in claim 17, further comprising a external charging station at which said storage capacitor can be charged.

19. The physiological sensor system as claimed in claim 7, wherein said power supply comprises at least one capacitor which is connected to coils that are arranged on an outside of said second shielded casing and deliver a voltage when an external magnetic field is applied.

20. The physiological sensor system as claimed in claim 19, further comprising at least one storage capacitor having a capacitance $\geq 1$ F which provides power during operation and can be recharged by said one or more solar cells during operation, said at least one storage capacitor being allocated to said solar cells or to said at least one capacitor.

21. The physiological sensor system as claimed in claim 20, further comprising a external charging station at which said storage capacitor can be charged.

22. The physiological sensor system as claimed in claim 7, wherein said signal transmission module is a radio transmission module based on one or more radio frequencies.

23. The physiological sensor system as claimed in claim 7, wherein said signal transmission module is an infrared transmission module having at least one infrared transmission diode with an allocated optical line.

24. The physiological sensor system as claimed in claim 7, wherein said signal transmission module is a fiber optic transmission module having at least one transmission diode with an allocated fiber optic line.

25. The physiological sensor system as claimed in claim 7, wherein said signal transmission module is an ultrasonic wave module having at least one ultrasound transducer.

26. The physiological sensor system as claimed in claim 7, further comprising an input for an external control line provided at said signal transmission module, control signals being looped through internal control lines from said signal transmission module to said signal conversion module.

27. The physiological sensor system as claimed in claim 26, further comprising an optical receiver which transforms optical control signals provided through an optical control line into electrical control signals, said optical receiver being allocated to a respective one of said internal control lines provided at said signal transmission module.

28. The physiological sensor system as claimed in claim 7, further comprising an ultrasound signal line arranged at said signal transmission module that is designed as an ultrasonic wave module, said ultrasound signal configured to transmit control signals which are transformed into electrical control signals by at least one ultrasound transducer provided on said signal transmission module.

29. A physiological sensor system for recording electrical measurement signals in an environment which impairs recording, comprising:
    a plurality of measurement electrodes;
    a signal amplifier device connected to one or more of said measurement electrodes;
    a power supply;
    an electronic device comprising a signal conversion device and an electronic signal transmission device that transmits to at least one of an external signal processing and a control instrument;
    a first shielded sensor casing arranged close to a patient having the following elements in or on said first shielded sensor casing: said measurement electrodes and said signal amplifier device;
    a second shielded casing arranged close to said patient having the following elements in said second shielded casing: said power supply and said electronic device, said signal amplifier device being connected or connectable to said electronic device and said power supply through at least one of a shielded cable connection and a twisted-wire cable connection; and
    at least one further sensor element which registers non-electrical measurement information, said at least one further sensor element being connected or connectable to said second casing, said electronic device comprising a converter for converting said non-electrical measurement information into electrical measurement signals.

30. The physiological sensor system as claimed in claim 29,
    wherein said at least one further sensor element is an optical sensor element;
    said physiological sensor system further comprising:
        at least one fiber optic line through which optical measurement information is sent to said electronic device; and
        an optoelectronic converter for conversion of said optical measurement information into electrical measurement signals.

31. The physiological sensor system as claimed in claim 30, wherein said optical sensor element is a finger ring.

32. The physiological sensor system as claimed in claim 29,
    wherein said at least one further sensor element is a pneumatic sensor element;
    said physiological sensor system further comprising:
        a pressure line through which said pneumatic sensor element is coupled to said electronic device; and
        a pressure sensor for conversion of pneumatic measurement information into electrical measurement signals.

33. The physiological sensor system as claimed in claim 32, wherein said pneumatic sensor element is a flexible chest ring.

* * * * *